US 7,599,822 B2

(12) United States Patent
Hearn et al.

(10) Patent No.: US 7,599,822 B2
(45) Date of Patent: Oct. 6, 2009

(54) PHYSIOCOCHEMICAL PROCESS MODELLING SYSTEM

(75) Inventors: Stephen Hearn, Dublin (IE); Andrew Bird, County Wicklow (IE); Joseph Hannon, County Wicklow (IE)

(73) Assignee: Dynochem IP Limited, Dublin (IE)

( * ) Notice: Subject to any disclaimer, the term of this patent is extended or adjusted under 35 U.S.C. 154(b) by 811 days.

(21) Appl. No.: 11/197,370

(22) Filed: Aug. 5, 2005

(65) Prior Publication Data

US 2005/0267723 A1  Dec. 1, 2005

Related U.S. Application Data

(63) Continuation of application No. PCT/IE03/00038, filed on Mar. 10, 2003.

(51) Int. Cl.
*G06F 17/10* (2006.01)
*G06F 7/60* (2006.01)
*G06G 7/58* (2006.01)
*G06G 7/48* (2006.01)

(52) U.S. Cl. .......................................... 703/2; 703/12
(58) Field of Classification Search .................. 703/2, 703/12
See application file for complete search history.

(56) References Cited

U.S. PATENT DOCUMENTS 5,740,033 A * 4/1998 Wassick et al. ............... 700/29
6,362,366 B1   3/2002 Hallinan et al. ............. 562/517
2001/0049595 A1  12/2001 Plumer et al. ................ 703/22
2002/0072828 A1   6/2002 Turner et al. ................ 700/269

FOREIGN PATENT DOCUMENTS

EP         0494110         8/1999
WO       WO01/71531       9/2001

OTHER PUBLICATIONS

"DOE/Opt: A System for Design of Experiments, Response Surface Modeling, and Optimization Using Process and Device Simulation", Boning et al. IEEE May 1994.*
Holm et al, Journal AWWA, vol. 90, Issue 7, Jul. 1998, pp. 80-89 Computing SI and CCPP using spreadsheet programs.
Lwin, Int J Engag Ed, vol. 16, No. 4, 2000, pp. 335-339, Chemical Equilibrium by Gibbs Energy Minimization on Spreadsheets.

* cited by examiner

*Primary Examiner*—Kamini Shah
*Assistant Examiner*—Saif Alhija
(74) *Attorney, Agent, or Firm*—Jacobson Holman PLLC

(57) ABSTRACT

A modelling system models a physicochemical process such as a chemical reaction process (1) with mass and heat transfers across liquid, gas, and solid phase boundaries. A model editor receives a components file (2(*a*)) of chemical species, a natural language process description, (2(*b*)), a scenarios file (2(*c*)) having multiple rows (records) each for a different set of conditions, and an experimental data file (2(*d*)). A validation function (24) parses the input files and also simultaneously automatically builds equations using rules associated with the process description. A simulator function executes a validated model comprising the built equations and data and integrates the equations by determining source and sink values at time steps.

22 Claims, 12 Drawing Sheets

Fig. 3 Heat Transfer utility: Vessel externals

| | A | B | C |
|---|---|---|---|
| 1 | | | |
| 2 | Name | MW | |
| 3 | heptane | 100 | |
| 4 | water | 18 | |
| 5 | A | 100 | |
| 6 | B | 117 | |
| 7 | P | 100 | |
| 8 | D | 117 | |
| 9 | OH | 17 | |
| 10 | | | |
| 11 | | | |

Fig. 7 Components sheet for Example 1.

| Phase/Flow | Identifier | [liquid/gas/solid] | |
|---|---|---|---|
| | [Temperature | value | C] |
| | [Pressure | value | Bar] |
| | [Density | value | kg/m³] |
| | [Cp | value | J/kgK] |
| | [Volume | unit] | |
| | [Mass | unit] | |
| | [Nmoles | unit] | |

[<variable list>], especially components present in this phase

*[The phase is the basic building block of a DynoChem model; e.g. reactions take place in a phase; mass transfer occurs between phases; values for pressure, CP, density, temperature needed for first phase and by default apply to others]*

| Cool with/Heat with | | Flow | [flow rate | Param] | [Flowout | flow2] |
|---|---|---|---|---|---|---|
| & | | | [UA | Param] | [UA(v) | Param] |

<Variable list>, especially coolant flowrate and inlet temperature

*[This statement cools the last phase mentioned]*

| Heat transfer of/Cool/Heat | [Phase] | with | Flow | [Flowout | flow2] | [flow rate | Param] |
|---|---|---|---|---|---|---|---|
| & | | | | [UA | Param] | [UA(v) | Param] |

<Variable list>, especially coolant flowrate and inlet temperature

*[This statement has identical meaning to 'Cool with/Heat with']*

| Heat exchange | Phase2 | [and | Phase] | [UA | Param] |
|---|---|---|---|---|---|
| <Variable list> | | | | | |
| Heat duty | param | [for | Phase] | | |

| Reactions [in | Phase] | | | | | | |
|---|---|---|---|---|---|---|---|
| [Reference Temperature/ T reference | | | value | | C/K] | | |
| | [k>/k0> | value | units] | [k</k0< | value | units] | |
| & | [Ea> | value | units] | [Ea< | value | units] | |
| & | [T ref | value | C/K] | [Reaction heat | value | units] | |
| & | * | | | | | | |
| & | N₁ Comp₁ | [+ | N₂ Comp₂] | >/= | N₁ Comp₁ | [+ | N₂ Comp₂] |

*[Note: entire reaction statement can appear on one row, see statements.xls]*

| Feed/In | Flow | [to | Phase] | [Flowrate | Param] | | |
|---|---|---|---|---|---|---|---|
| <Variable list>, especially components and flowrate | | | | | | | |
| Remove/Out | Flow | [from | Phase] | [Flowrate/residence time | Param] | [Min Volume | Param] |
| <Variable list>, especially flowrate or residence time | | | | | | | |
| Transfer to | Phase2 | [from | Phase] | [Flowrate/residence time | Param] | [Min Volume | Param] |
| <Variable list>, especially flowrate or residence time | | | | | | | |

| Mass exchange | [disperse] | Phase2 | [and | Phase] | | | |
|---|---|---|---|---|---|---|---|
| | [K₁a/K₁a/K₁a | value | | Unit] | | | |
| | [K₁a/K₁a | value | | Unit] | | | |
| | Thermo | [Henry | value] | | | | |
| | | [C*/Cstar | value | value2 | unit] | | |
| | | [P*/Pstar/Pvap | value | unit] | | | |
| | | [Cd/Cc | value] | | | | |
| | | [xd/xc | value] | | | | |
| | | [Antoine | A | B | C | [log10] | [units] ] |
| | | [H transfer | value | unit] | | | |
| | | [H vap | value | unit] | | | |
| | | [H crystal | value | unit] | | | |

| Variables | | | | | |
|---|---|---|---|---|---|
| [<variable list>], user-defined, without phase name | | | | | |
| Calculate | [<Expression>] | | | | |
| [<expression list>] | i.e. phase.variable/component/parameter.attribute:= | | | function | |
| Integrate | comp | of | flow | to | Param |

Fig. 8

|   | A | B | C | D | E | F | G | H | I | J | K |
|---|---|---|---|---|---|---|---|---|---|---|---|
| 1 |   |   | HOW HETEROGENEITY CAN INFLUENCE SELECTMTY | | | | | | | | |
| 2 |   |   |   |   |   |   |   |   |   |   |   |
| 3 |   | PHASE | Aqueous | Liquid |   |   |   |   |   |   |   |
| 4 |   |   | pressure | 1 | bar |   |   |   |   |   |   |
| 5 |   |   | temperature | 20 | C |   |   |   |   |   |   |
| 6 |   |   | CP | 4.2 | KJ/Kg |   |   |   |   |   |   |
| 7 |   |   | Density | 1000 | Kg/m3 |   |   |   |   |   |   |
| 8 |   |   | water |   | kg |   |   |   |   |   |   |
| 9 |   |   | A |   | mol | plot |   |   |   |   |   |
| 10 |   |   | P |   | mol | plot |   |   |   |   |   |
| 11 |   |   | D |   | mol | plot |   |   |   |   |   |
| 12 |   |   | OH |   | mol | plot |   |   |   |   |   |
| 13 |   |   | volume |   | m3 |   |   |   |   |   |   |
| 14 |   |   |   |   |   |   |   |   |   |   |   |
| 15 |   | PHASE | Organic | Liquid |   |   |   |   |   |   |   |
| 16 |   |   | pressure | 1 | bar |   |   |   |   |   |   |
| 17 |   |   | temperature | 20 | C |   |   |   |   |   |   |
| 18 |   |   | CP | 4.2 | KJ/Kg |   |   |   |   |   |   |
| 29 |   |   | Density | 1000 | Kg/m3 |   |   |   |   |   |   |
| 20 |   |   | A |   | mol | plot |   |   |   |   |   |
| 21 |   |   | P |   | mol | plot |   |   |   |   |   |
| 22 |   |   | heptane |   | kg |   |   |   |   |   |   |
| 23 |   |   | volume |   | m3 |   |   |   |   |   |   |
| 24 |   |   |   |   |   |   |   |   |   |   |   |
| 25 |   | Master Transfer | Organic | and | Aqueous | name | MTI |   |   |   |   |
| 26 |   |   | KLa | 1 | 1/s |   |   |   |   |   |   |
| 27 |   |   | Kda | 1 | 1/s |   |   |   |   |   |   |
| 28 |   |   | A | phase eqm | Cd/Cc | 1 |   |   |   |   |   |
| 29 |   |   | P | phase eqm | Cd/Cc | 100 |   |   |   |   |   |
| 30 |   |   |   |   |   |   |   |   |   |   |   |
| 31 |   | Reaction In | Aqueous |   |   |   |   |   |   |   |   |
| 32 |   | Rxn1 | k> | 0.01 | L/mol s | . | A | + | OH | > | P |
| 33 |   | Rxn2 | k> | 0.0001 | L/mol s | . | P | + | OH | > | D |
| 34 |   |   |   |   |   |   |   |   |   |   |   |
| 35 |   | Finished |   |   |   |   |   |   |   |   |   |

Fig. 9 Process sheet for Example 1.

| | A | B | C | D | E | F | G | H | I |
|---|---|---|---|---|---|---|---|---|---|
| 1 | | Items | | Aqueous | Aqueous | Organic | Organic | Organic | Organic | MT1 |
| 2 | | Variables | | water | OH | heptane | A | KLa | Kda | A.CdCc |
| 3 | | Units | | kg | mol | kg | mol | 1/s | 1/s | - |
| 4 | | | | | | | | | | |
| 5 | Partition A org/aq = 1, kLa = kda = 1 | 1duration | 0.75 | 1 | 0.6255 | 1 | 1 | 1 | 1 |
| 6 | Partition A org/aq = 1, kLa = kda = 0.1 | 1duration | 0.75 | 1 | 0.6255 | 1 | 0.1 | 0.1 | 1 |
| 7 | Partition A org/aq = 1, kLa = kda = 0.01 | 1duration | 0.75 | 1 | 0.6255 | 1 | 0.01 | 0.01 | 1 |
| 8 | Partition A org/aq = 10, kLa = kda = 1 | 1duration | 0.75 | 1 | 0.6255 | 1 | 1 | 1 | 10 |
| 9 | Partition A org/aq = 10, kLa = kda = 1 | 1duration | 0.75 | 1 | 0.6255 | 1 | 0.1 | 0.1 | 10 |
| 10 | Partition A org/aq = 10, kLa = kda = 1 | 1duration | 0.75 | 1 | 0.6255 | 1 | 0.01 | 0.01 | 10 |
| 11 | Partition A org/aq = 100, kLa = kda = 1 | 2duration | 0.75 | 1 | 0.6255 | 1 | 1 | 1 | 100 |
| 12 | Partition A org/aq = 100, kLa = kda = 0.1 | 2duration | 0.75 | 1 | 0.6255 | 1 | 0.1 | 0.1 | 100 |
| 13 | Partition A org/aq = 100, kLa = kda = 0.01 | 2duration | 0.75 | 1 | 0.6255 | 1 | 0.01 | 0.01 | 100 |
| 14 | Partition A org/aq = 1000, kLa = kda = 1 | 2duration | 0.75 | 1 | 0.6255 | 1 | 1 | 1 | 1.00E+03 |
| 15 | Partition A org/aq = 1000, kLa = kda = 0.1 | 3duration | 0.75 | 1 | 0.6255 | 1 | 0.1 | 0.1 | 1.00E+03 |
| 16 | Partition A org/aq = 1000, kLa = kda = 0.01 | 3duration | 0.75 | 1 | 0.6255 | 1 | 0.01 | 0.01 | 1.00E+03 |

Fig. 10 Scenarios sheet for Example 1.

| | A | B |
|---|---|---|
| 1 | | |
| 2 | | Organic |
| 3 | Time | P |
| 4 | min | mol |
| 5 | 0 | 0 |
| 6 | 2 | 0.3908 |
| 7 | 12 | 0.8223 |
| 8 | 24 | 0.8983 |
| 9 | 37 | 0.9267 |
| 10 | 49 | 0.9415 |
| 11 | 61 | 0.9506 |
| 12 | 73 | 0.9567 |
| 13 | 86 | 0.9612 |
| 14 | 98 | 0.9645 |
| 15 | 110 | 0.9671 |
| 16 | 122 | 0.9692 |
| 17 | 135 | 0.971 |
| 18 | 147 | 0.9724 |
| 19 | 159 | 0.9736 |
| 20 | 171 | 0.9747 |
| 21 | 184 | 0.9756 |
| 22 | 300 | 0.9805 |

Fig. 11 A Data sheet from Example 1.

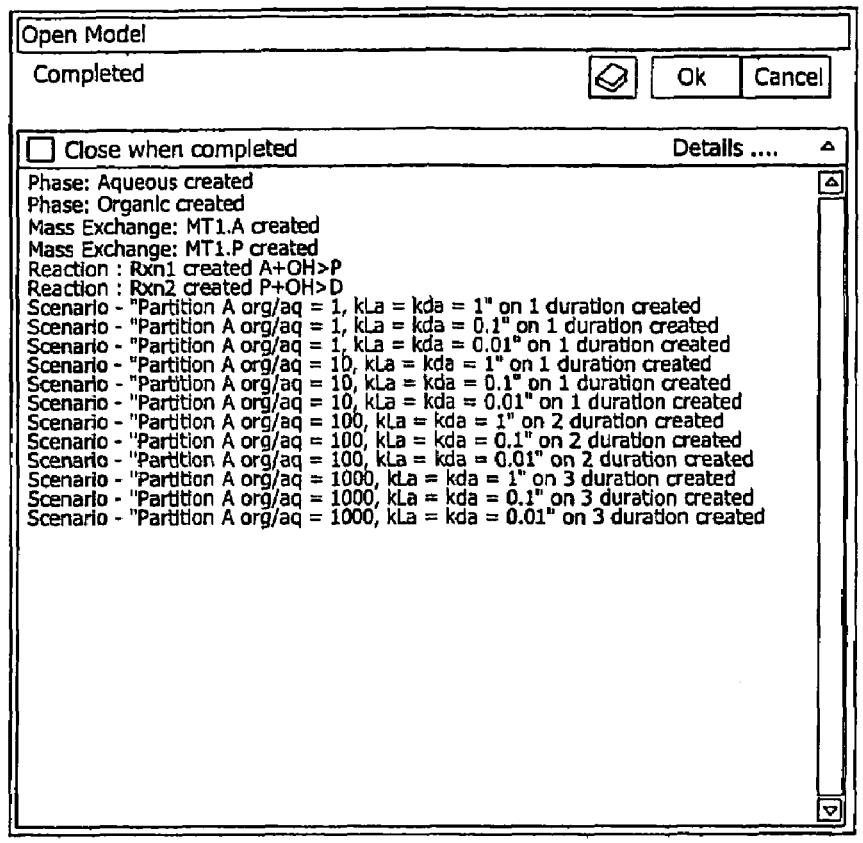
Fig. 12 Parser report for Example 1.
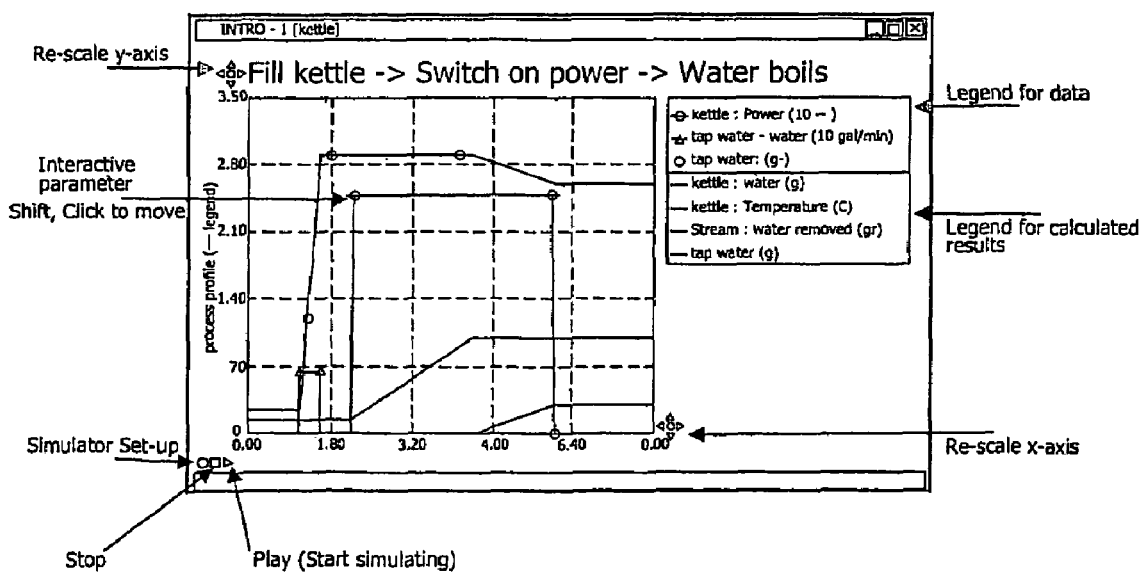
Fig. 13

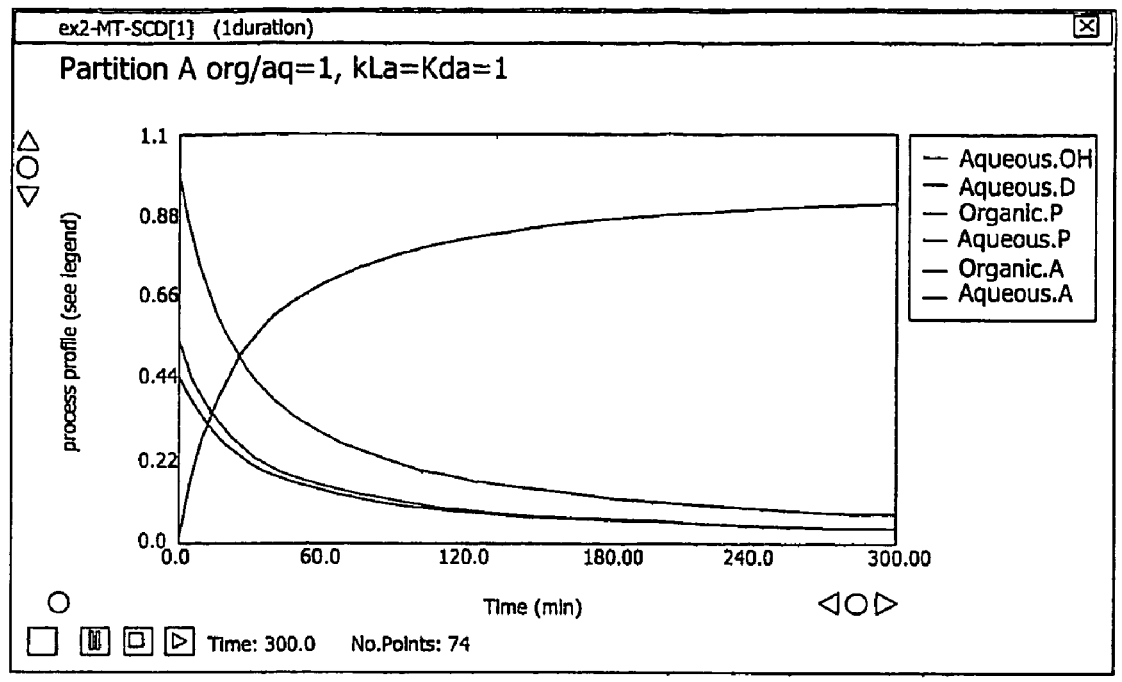
Fig. 14 Visualised display of a Simulation of Example 1.
Fig. 15 Simulated outputs from Example 1.

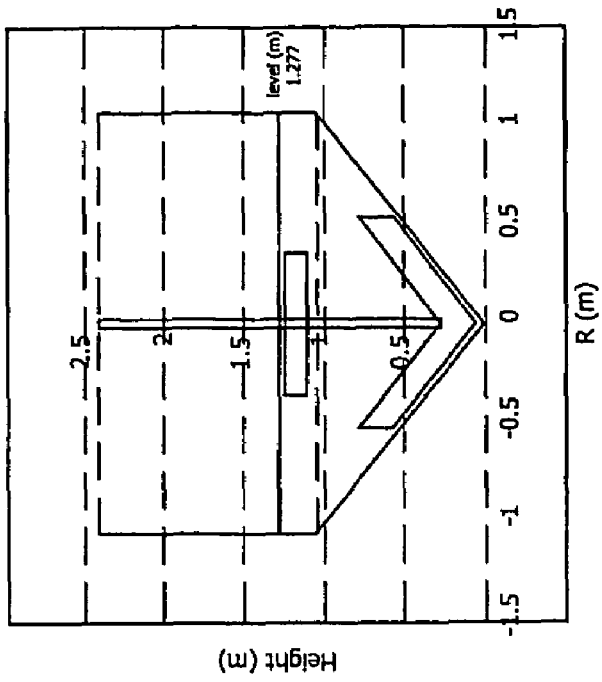
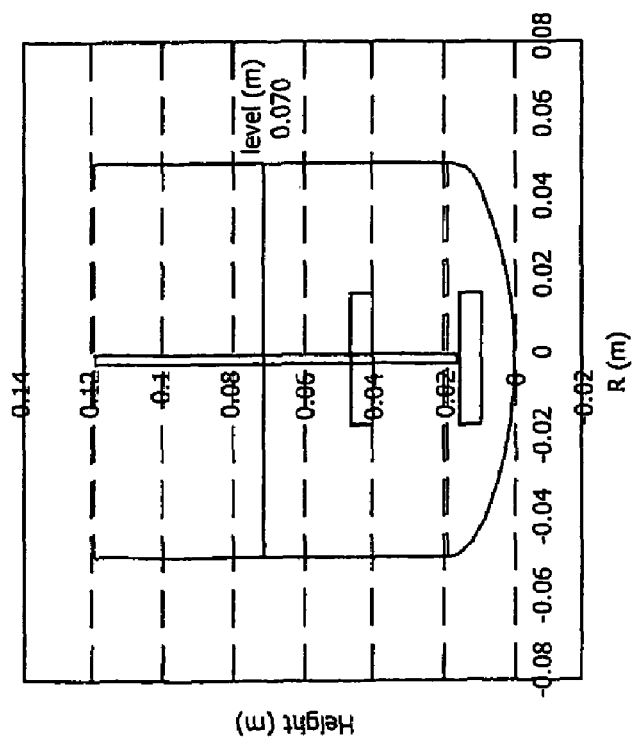
Fig. 16

PHYSIOCOCHEMICAL PROCESS MODELLING SYSTEM

This is a continuation of PCT/IE03/000038 filed Mar. 10, 2003 and published in English.

INTRODUCTION

1. Field of the Invention

The invention relates to modelling of processes which involve manipulating chemical species such as by chemical reactions, mass transfers, phase transfers, or flows. Such processes are referred to in this specification under the general term "physicochemical processes".

2. Prior Art Discussion

Physicochemical processes by their nature are very complex, with significantly different results arising from what appear to be slight variations in process parameters. Using laboratory experiments alone to develop new processes is a time-consuming approach often based on intuition and trial-and-error rather than understanding and scientific principles, even when many of these principles are well established. Laboratory experiments by their very nature are limited to the small scale and cannot reproduce all the features of industrial scale equipment. Processes that are inherently feasible at the industrial scale can be rejected at an early stage because of poorly understood results from laboratory glassware. Conversely, excellent results produced easily in the laboratory can take years of development to become commercially viable on scale-up.

This problem has been addressed by use of computer modelling or simulation. European Patent Specification No. EP1266339 describes a method of analysing chemical processes. In this approach, a chemical model is selected and thermodynamic property data and chemical equilibrium prediction data are generated. European Patent Specification No. EP0494110 describes a process for the estimation of physical properties of a proposed polymer. The approach is to model the physical polymer structure based on input data.

The invention is directed towards providing for more comprehensive modelling of physicochemical processes in a manner that is easy to use.

SUMMARY OF THE INVENTION

According to the invention, there is provided a physicochemical process modelling system comprising a data processor, a user input interface, an output interface, a memory, and a data storage device, wherein, the storage device stores a library of initial models each having code for modelling a physicochemical process;

the processor is programmed with:
  a model editor having an input interface for prompting user input of chemical species component data, a process description, and experimental data, the process description being in a natural language,
  a validation function for parsing the inputs, for performing semantic, contextual, consistency, and tolerance checks, and for automatically building equations according to rules associated with the process description,
  a simulator function for executing and integrating the equations built by the validation function,
  a fitting function for operating exclusively with data of the edited and validated model to fit physical and/or chemical rate constants to achieve a best fit with the experimental data, and
  an optimisation function for iteratively executing the fitted model with different process condition inputs until an output parameter such as product yield is optimised to a maximum value or a parameter such as waste byproduct yield is optimised to a minimum value.

In one embodiment, the initial model library has a hierarchical structure with initial models at leaf nodes of the structure and physicochemical selection criteria at upper levels of the structure.

In another embodiment, the model editor interface receives the component, process, and experimental data in separate but linked input files.

In a further embodiment, the model editor interface also receives a scenarios input file specifying options for implementing specific cases of the generic process input file.

In one embodiment, each record of the scenarios file specifies a combination of vessel parameters and values of temperature, pressure and process recipe.

In another embodiment, the experimental data file is linked to the other files, and the model editor can use the data from the experimental data file in preference to data of the other files.

In a further embodiment, the model editor interface provides a dictionary of phrases having meanings recognised by the system, and allows phrases to be cut and pasted into the process description.

In one embodiment, the phrases include phrases identifying a rate of change, or a type of phase or flow for physicochemical process modelling.

In another embodiment, the model editor interface allows user setting of attributes of variables including:
  a 'plot' attribute, causing the associated variable to be plotted during modelling, and
  an 'impose' attribute, causing the associated variable to be treated as active data, which participate in the execution of a model and include imposed operating conditions such as a reactant addition flow rate, temperature or species quantity or concentration.

In a further embodiment, the validation function builds equations describing the physicochemical process by:
  parsing the inputted components and building a database of valid component names and properties;
  parsing phase data of the process description and building a database of valid phase names and states;
  parsing flow statements of the process description and building a database of valid flow names and states, and automatically assigning a differential equation to each component or temperature involved in the process description and adding a corresponding source or sink term to the equation.

In one embodiment, the validation function stores a validated model as the developed equations with parameters from the component and process description received by the model editor.

In another embodiment, the validation function stores a validated model with a plurality of input conditions in a scenarios file with its associated experimental data.

In a further embodiment, the validation function recognises flow and phase inputs by parsing pre-defined statements followed by flow or phase inputs.

In one embodiment, the simulator function integrates the equations of a validated model by ensuring that there is mass and energy conservation and that rates are consistent.

In another embodiment, the simulator calculates all sources and sinks of each equation at each of a plurality of time steps.

In a further embodiment, the simulator function comprises a plurality of solvers, each suitable for a particular validated model.

In one embodiment, the fitting function selects to fit model parameters to the whole, only part of, or multiple series of experimental data.

In another embodiment, the fitting function resets in response to a user input and re-executes using fresh experimental data received by the model editor and validated by the validation function.

In a further embodiment, the fitting function operates ignoring parameters which are indicated as being switched off in the process description.

In one embodiment, the system further comprises a vessel fit function for assessing suitability of a vessel for the physicochemical process being modelled according to vessel characteristics.

DETAILED DESCRIPTION OF THE INVENTION

Brief Description of the Drawings

The invention will be more clearly understood from the following description of some embodiments thereof, given by way of example only with reference to the accompanying drawings in which:

FIG. 7 is a sample components sheet of a model from Example 1;

FIG. 8 is a set of natural language statements that represent a range of physicochemical mechanisms, to define the process description of the model;

FIG. 9 is a sample process sheet of a model from Example 1;

FIG. 10 is a sample scenarios sheet of a model from Example 1;

FIG. 11 is a sample data sheet from Example 1;

FIG. 12 is a log of the transformation of the input files containing natural language statements into differential equations (from Example 1);

FIG. 13 is a generic graphical representation of integrated results;

FIG. 14 is a sample screenshot of model integrated results from Example 1;

FIG. 15 is a snapshot display of the contents of the phases in the model (Example 1); and FIG. 16 is a sample display of the system showing reaction vessel parameters.

DESCRIPTION OF THE EMBODIMENTS

Figure 1:
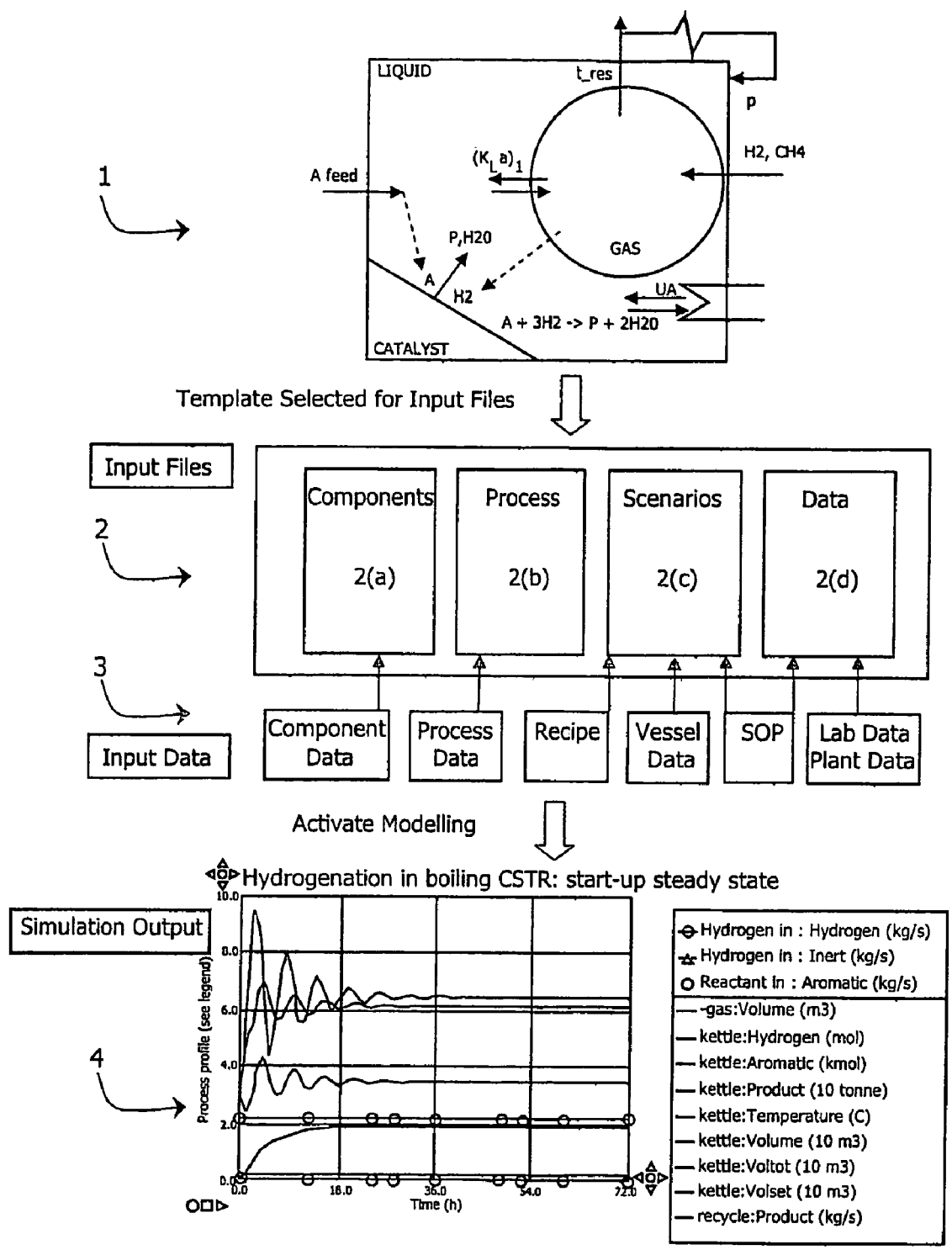
FIG. 1 is a diagram showing at a high level operation of a modelling system of the invention.

Referring to FIG. 1 aspects of a chemical process are represented diagrammatically by the numeral 1. This diagram shows chemical and heat transfers across liquid, gas, and catalyst phase boundaries. A modelling system of the invention generates with user inputs a set of input files or sheets 2 in spreadsheet format. The files 2 include Components 2(a), Process 2(b), Scenarios 2(c), and Data 2(d) files. Input data 3 for the system includes:

component data for the file 2(a);
process data for the files 2(b);
chemical recipe data for the files 2(c);
vessel characterisation data for the file 2(c);
standard operating procedure (SOP) data for the files 2(c) and 2(d); and
laboratory and plant data for the file 2(d).

Operation of the modelling system is in response to user activation using the input files 2, and the output is a simulation such as indicated by 4 for a continuous hydrogenation in a boiling reactor from start-up to steady state.

The major operating modes of chemical and biochemical industry equipment can be modelled by the system. These include: continuous operation (predominant in the petrochemicals and bulk chemicals industries; as indicated by 4); semi-continuous operation (common in the speciality and fine chemicals industries); batch and fed-batch operation (the favoured operation of bioreactors and of high-value chemicals such as pharmaceuticals).

Figure 2:
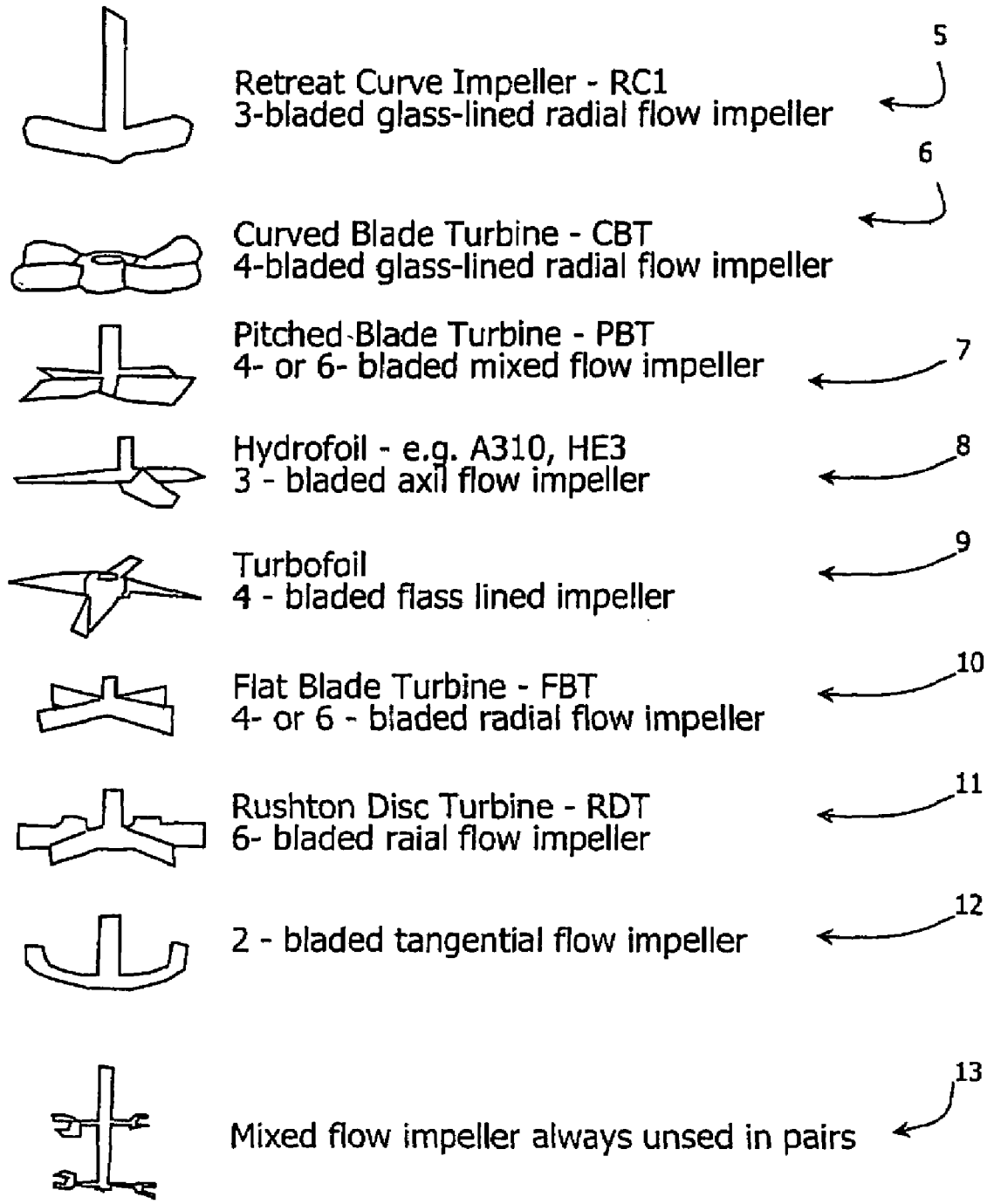
FIG. 2 is a set of diagrams of process equipment internals, the operation of which are modelled for example by the system.

As an indication of the range of equipment and different types of vessel which may be modelled, FIG. 2 illustrates diagrammatically and describes a set of vessel impellers as follows:

5: retreat curve impeller;
6: curved blade turbine;
7: pitched blade turbine;
8: hydrofoil;
9: turbofoil;
10: flat blade turbine;
11: Rushton disc turbine;
12: tangential flow impeller; and
13: pair of mixed flow impellers.

The user can select multiple impellers in the same vessel in addition to defining their own characteristics for impellers not included in the list. The impeller configuration defines the vessel agitator and the mechanical component of vessel internals. The system also encompasses non-moving, physical internals, such as wall baffles, beavertail baffles, cooling coils and dip pipes.

Figure 3:
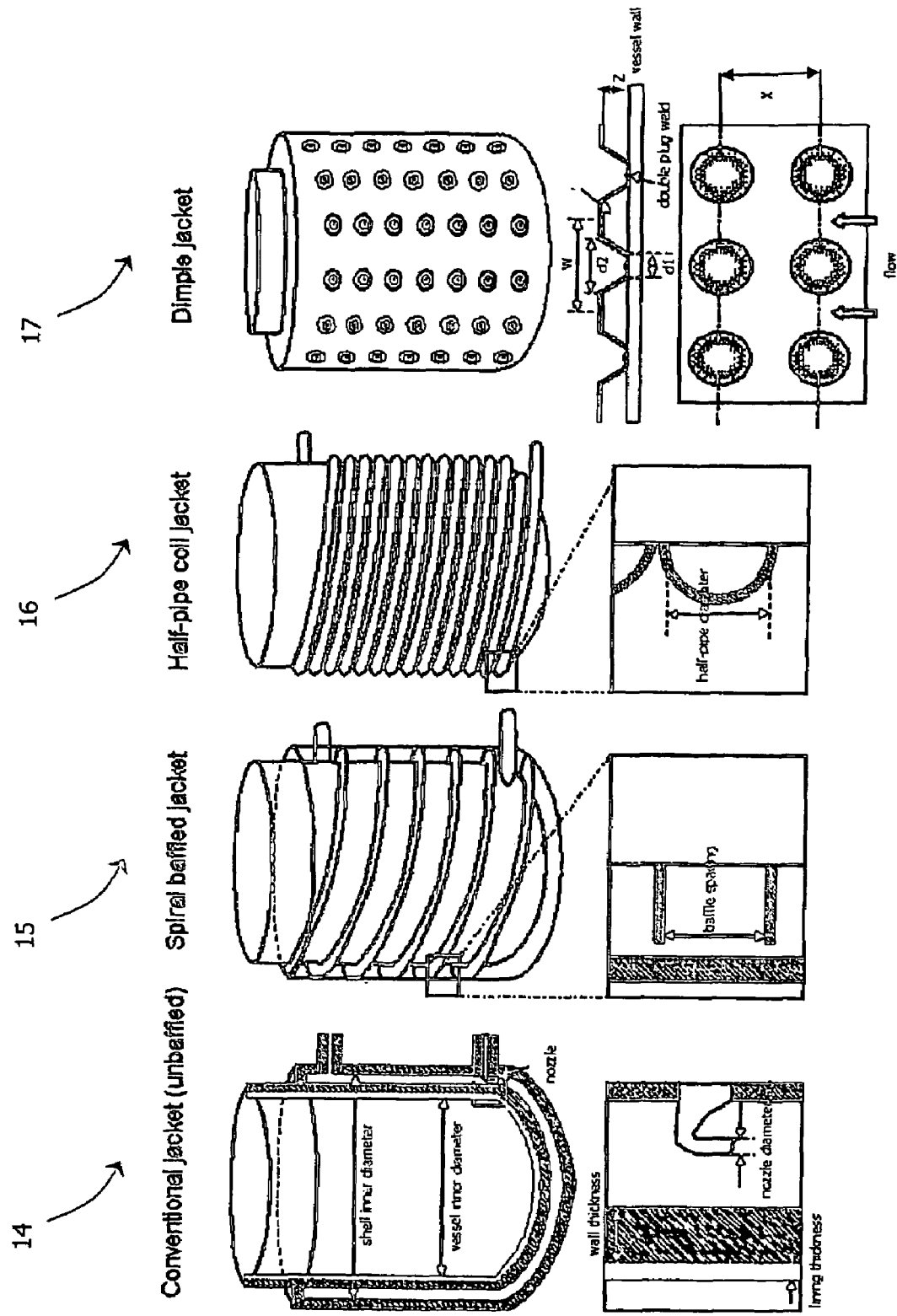
FIG. 3 is a set of diagrams of process equipment externals, the operation of which are modelled for example by the system.

FIG. 3 illustrates diagrammatically and describes a set of vessel externals that are also incorporated within the system:

14: conventional (unbaffled) jacket;
15: spiral baffled jacket;
16: half-pipe coil jacket; and
17: dimple jacket.

The measurements of instrumentation probes within the vessel are also modelled. Probes relate to in situ devices such as: thermocouples (for temperature measurement), pressure transducers (in a vessel's headspace), flow control valves (for reactant additions), species monitoring (e.g. infra red (IR) data for component concentrations) and particulate measuring devices (e.g. FBRM probe).

The system is also capable of modelling the control system of the vessel. Using predicted or imposed instrumentation data as input, with a description of the controller's programmable logic, e.g. proportional, integral, differential (PID) control settings, the model predicts the response of the vessel to dynamically changing operating conditions and disturbances. The system therefore comprises a detailed, multi-level description of a process operation through characterisation of the vessel operating mode, vessel internals, vessel externals, in situ instrumentation and the vessel control settings.

Figure 4:
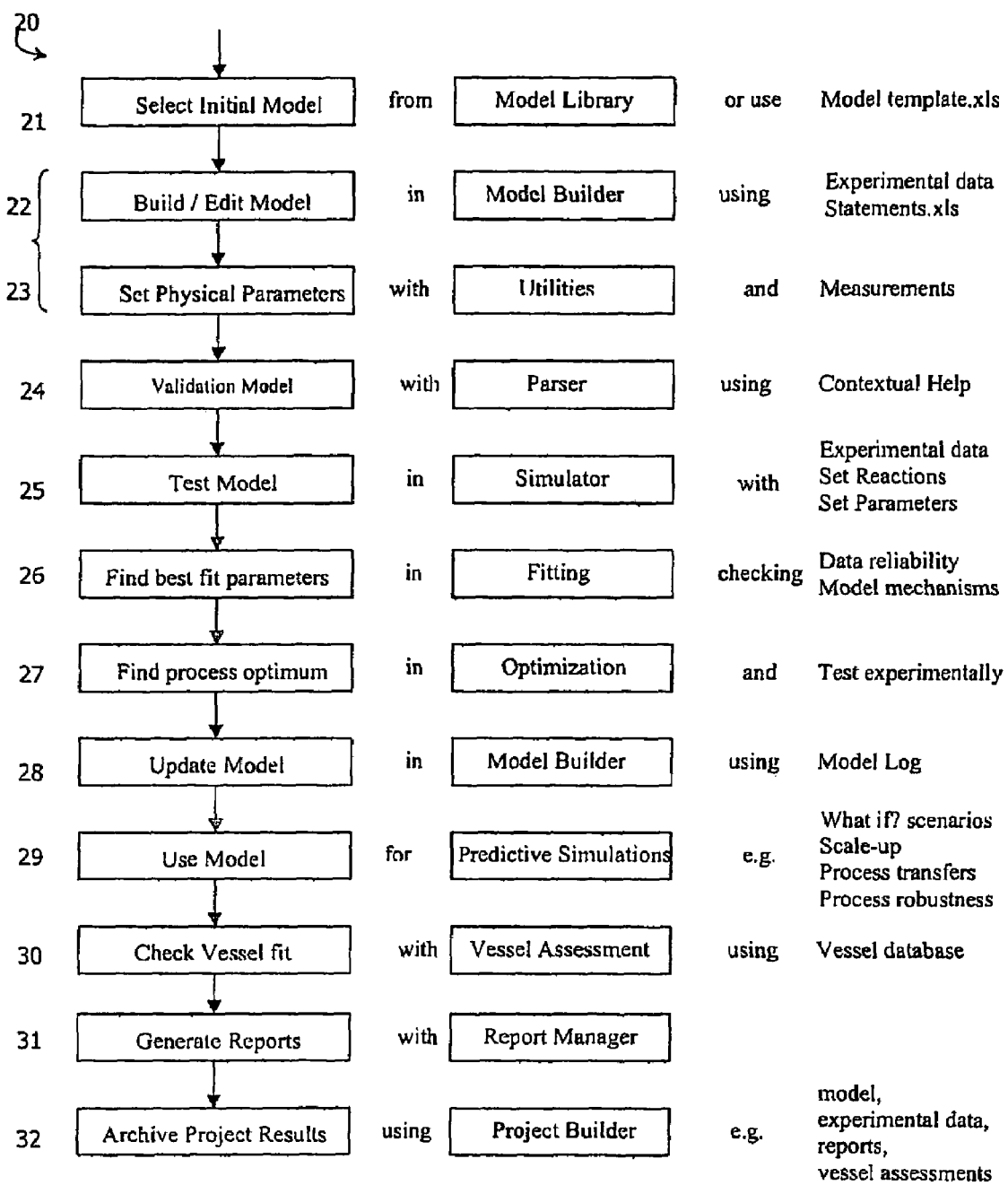
FIG. 4 is a flow diagram of operation of the system in more detail.
Figure 5:
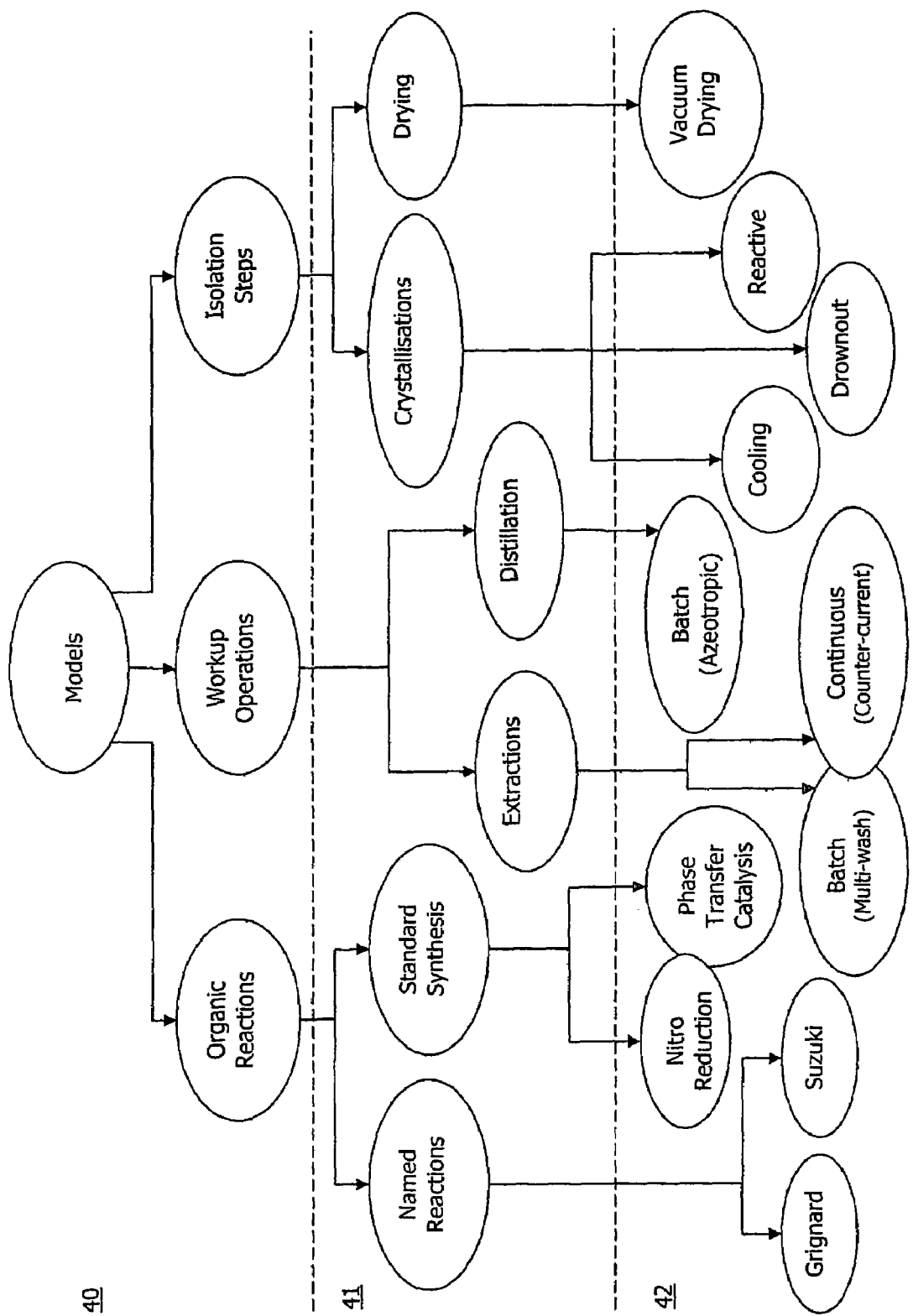
FIG. 5 is a diagram illustrating structure of a model library of the system.

The system is most clearly described by way of a description of its operation, with reference to FIGS. 4 and 5 initially. A method 20 of operation of the system is illustrated in FIG. 4 as a series of steps 21 to 32 inclusive.

21: Select Initial Model

The system stores a model library, in which the models are leaf nodes 42 of a hierarchical structure, part of which is illustrated in FIG. 5. The user navigates through a menu structure 40 and 41 having, from top down, model templates organised according to selection criteria for physicochemical processes such as batch processing in drug substance manufacture.

This structure is particularly effective because an initial model for most synthesis reaction or work-up and isolation step may be quickly found and adapted by the user to a specific application. Of particular importance are reaction steps such as hydrogenation and isolation steps such as crystallizations. Crystallisation is the ubiquitous method for producing and controlling the form of a final drug substance and so is a major selection criterion. The system enables users to model these steps at several levels of detail, including safety studies, yield optimisation, impurity minimisation and control of crystal size distribution, an essential feature for FDA approval of drug substance manufacturing processes.

Figure 6:
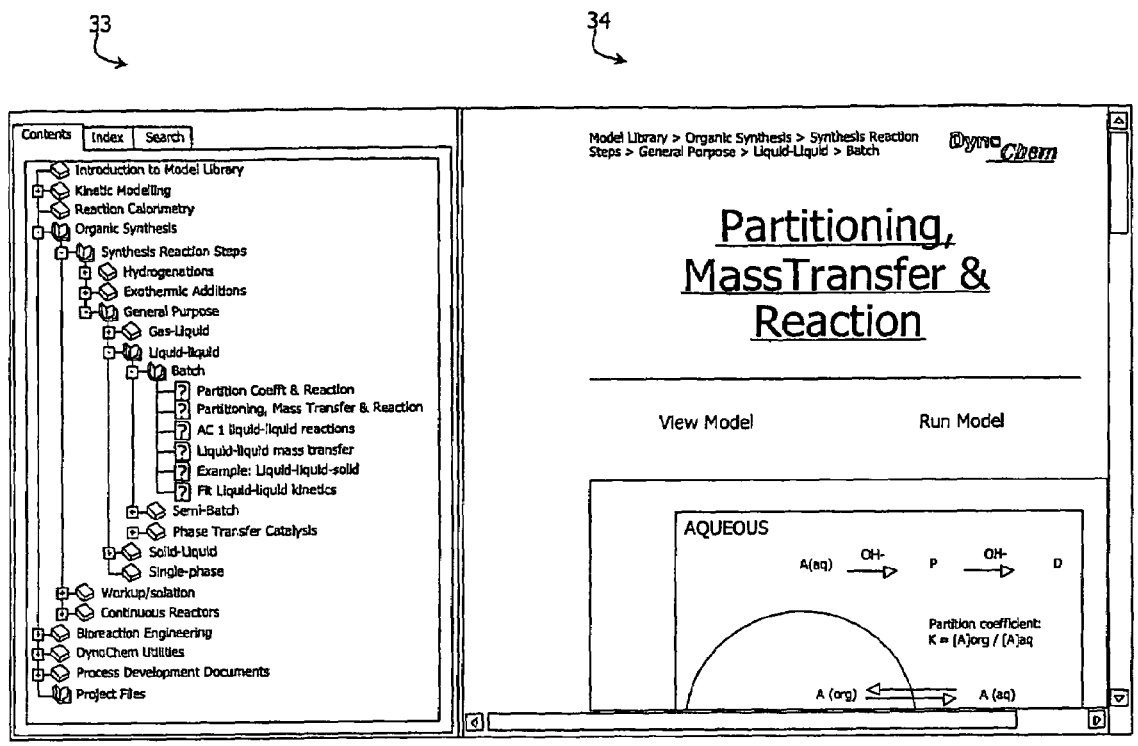
FIG. 6 is a sample hierarchical tree display based on a process scheme search and an example leaf node for a model from the library.

FIG. 6 is a view of a sample model, as displayed by the modelling system in the library. This diagram illustrates a particular navigation structure 33 and the template model 32 ready for editing by the user.

22: Edit Model and 23: Set Physical Parameters

The model editor has an interface which displays the various sheets for user input of data to create the input data files 2(*a*) to 2(*d*). Step 22 comprises four primary sub-steps namely: i) editing the components sheet 2(*a*) based on the chemical species that exist in the process; ii) editing the model process sheet 2(*b*), adding and removing phases and rate processes using a familiar natural language; iii) editing the model scenarios sheet 2(*c*), entering details of conditions for each scenario to be modelled; and iv) editing experimental data sheets 2(*d*), including data and other profiles as a function of time.

As shown in FIG. 7 for Example 1, a component sheet 2(*a*) lists the chemical species for the process together with their molecular weights ("MW"). The user is allowed to add component data in rows of this sheet including, for certain applications, the sub-group composition of molecules for modelling non-ideal behaviour using the UNIFAC method.

As shown in FIG. 8, the process sheet 2(*b*) lists phases and rate processes considered by the user to be relevant to a chemical process based on knowledge, experience with similar systems and comparison with experimental data. The syntax used to represent these features is selected from a dictionary of words and phrases stored in the system, as a spreadsheet file called "Statements". The user simply selects appropriate natural language statements by cutting and pasting from this file.

FIG. 9 shows a process sheet 2(*b*) for Example 1, a batch oil-water reaction system. The process sheet 2(*b*) describes two immiscible phases (organic and aqueous), the mass transfer between the phases for two components and two chemical reactions in the aqueous phase.

A sample scenarios sheet 2(*c*) for Example 1 is shown in FIG. 10. Each row is a specific set of conditions such as temperature, pressure, recipe. "Drilling down" at a particular row accesses the relevant data sheet 2(*d*) and any data profiles associated with the scenario. An example data sheet 2(*d*) is shown in FIG. 11. The data sheet 2(*d*) contains two primary types of data, namely:

passive data, being results from actual experiments that do not influence the execution of the model when used in either the simulator and optimisation functions, and active data, which participate in the execution of a model and include imposed operating conditions such as a reactant addition flow rate and results from actual experiments when used in the parameter fitting function.

Supporting engineering calculations (for example minimum agitation requirements and heat transfer coefficients) and physical property estimates for common solvents are available in the system. These system or vessel characteristics may be entered in step 23 on the scenarios sheet 2(*c*) when they vary between scenarios, e.g. between laboratory and larger scale conditions. The system has utilities to support responsible and successful usage of simulation in process development and scale-up. A wide range of Imperial, US and SI units can be used. The system converts all inputs to SI (moles, kilograms, seconds, Kelvin, Joules, etc.) for all internal calculations, but the user can view model values in units of their choosing.

Referring to the input files 2(*b*), 2(*c*), 2(*d*) (of FIG. 1) the system expects the following information for all variables: phase name, variable name, value (can be blank) and units. Values can be left blank on the process sheet 2(*b*) if they are subsequently supplied on the scenarios or data sheets 2(*c*) and 2(*d*). Values in data sheets 2(*d*) over-ride values in process and scenarios sheets 2(*b*) and 2(*c*). Attributes for variables may also be set, to guide the treatment of each variable in the model editor function as follows, for example:

Plot (profile for variable will appear when the simulation begins);

Monitor (profile will be stored for plotting but will not be plotted automatically);

Adjust (value of variable may be changed in the system);

Interactive or Impose (profile of variable will be imposed on the model by reading from a datasheet and may be changed by dragging points on screen in the external executable);

Link2data (profile of variable will be imposed on the model by reading a profile from a data sheet); and Vary (a differential equation for the variable will be set up for which the user may supply initial values, sources or sinks).

User-defined variables may be added to the model on the process sheet 2(*b*) using the 'Variables' keyword of the natural language. These may then be used in other sheets of the model and in 'Calculate' statements to evaluate expressions. Available functions for use in Calculate Statements functions include:

concentration, accessed as conc (phase.component);

rate of change, accessed as phase.variable.dNdt;

activity coefficient, accessed as phase.component.gamma; and max( ), min( ), if( ), data( ), where data( ) allows profiles on the corresponding data sheet to be used directly in model calculations.

The model editor function processes the completed components, process, scenarios, and data sheets to complete the model for initial simulation. This model is based on phases providing the structure, and rate processes taking place at and between phase boundaries as shown in FIG. 1.

24: Validation

In this step a validation function of the system validates the model's natural language inputs by a parser parsing the components, process, scenarios and data files and performing semantic, contextual, consistency and tolerance checks. Any errors are highlighting in a parser report file, which the user may view before making corrections. FIG. 12 shows sample a parser report file for the successful completion of parsing for Example 1.

While parsing and validating, the system builds equations to describe the chemical process as defined by the user's natural language inputs on the process sheet 2(b). The equations created are of the form:

$$dNi/dt = \text{sources} - \text{sinks 'differential'},$$

where Ni can be any variable, but is most frequently the number of moles of a component i;

or $$y = f(x) \text{ 'algebraic'}.$$

Batch, fed-batch, continuous and semi-continuous reactors are dynamic systems and differential equations are required to describe the rate of change of many variables with time, with suitable coupling between equations whose variables affect each other. These equations are primarily applied to components and temperature in each fluid 'phase' and are created from natural language paragraphs on the process sheet 2(b), such as:

Entities of FIG. 8 to which variables will belong:
Phase . . . statements set up the phases to which species and other variables belong;
Flow . . . statements set up flows to which species and other variables belong.

Statements of FIG. 8 resulting in the calculation of rate processes (sources and sinks):
Feed . . . statements connect flows to phases, causing material to enter a phase;
Remove . . . statements connect phases to flows, causing material to leave a phase;
Transfer to . . . statements connect phases to phases, causing movement of material between the phases;
Reactions in . . . statements set up chemical transformations in a phase, causing some species to reduce in concentration and others to increase;
Mass Exchange . . . statements connect phases to phases causing movement of material between phases due to mixing;
Heat transfer . . . statements connect flows to phases causing movement of thermal energy between the flow and the phase; and
Heat exchange . . . statements connect phases to phases causing movement of thermal energy between phases due to mixing.

Each of the above 'statements' entered by the user on the process sheet 2(b) defines a rate process that involves at least one phase or flow and one component and in many cases several components and an associated energy term. In general the left hand side of each equation is denoted Variable.dndt and the right hand side assembled internally by the program is of arbitrary length, depending on the number of rate processes affecting the variable.

Such an equation set very quickly becomes unwieldy and difficult to write, read, share, modify or solve by any normal programming or model development system. In the present system, the user can focus on adding and removing components (into the file 2(a)) and rate processes such as additional reactions (into the file 2(b)) in line with their own chemical or physical intuition, thereby developing a better understanding and description of their system, while the system automatically creates the necessary additional equations and appends the resulting sources and sinks to all affected equations, then solving the full set of integrated equations and displaying the results.

The statements define 'parameters' from which the strength of each source and sink is automatically calculated. These parameters may be the subject of algebraic equations and so may also be time-dependent.

Algebraic equations are built from the process sheet 2(b) using the following language of FIG. 8:
Variables . . . statement which allows the user to define the necessary new variable names and their units of measure; and
Calculate . . . statement which allows the user to define the equation from which the variable will be calculated.

For this purpose, the definition of a variable is any parameter that can be accessed using the natural language, including the rate of change of any variable for which a differential equation is being solved. So, for example, the rate of change of the number of moles of species A may already be affected by feeding, removal, mass exchange, reactions and a further source or sink can be added using a Calculate statement:

$$\text{Phasename}.A.dndt := \text{Phasename}.A.dndt + X$$

where X is the additional term.

Equations defined using the above statements are read by the system and solved at every step of the dynamic simulation, with full coupling where relevant to the differential equations in the model. All of the equations of the model are built by the validation function as the process sheet is parsed and checked. First the parser reads the components sheet 2(a) and builds a database of valid component names and properties for usage in the model. The parser then reads the process sheet 2(b) systematically as follows.

When a 'phase' statement is found, it appends the phase name FIG. 8 to an internal database of valid phase names and states for usage in the model. A phase will be an entity to which variables (components, temperature, pressure) may belong. The statement itself does not result in the creation of any equations.

Subsequent rows on the process sheet 2(b) may optionally define the initial values of variables related to that phase FIG. 8, their user-defined units (must be a valid combination of SI, Imperial or US units, by reference to the pre-defined but user-modifiable units database) and user-defined attributes for the variable, primarily whether it will be:
plotted automatically when the system executes the simulation; or
subject to a rate equation (this is default for species and temperature); or
imposed on the calculation as a response/solution variable.

When a 'flow' statement is found (cfr. FIG. 8), the system appends the flow name to a database of valid flow names and states for usage in the model. A flow will be an entity to which variables (components, temperature, pressure) may belong. The statement itself does not result in the creation of any equations. Subsequent rows may optionally define the values of variables related to that flow, their user-defined units (must be a valid combination of SI, Imperial or US units, by reference to the pre-defined but user-modifiable units database) and user-defined attributes for the variable, primarily whether it will be plotted automatically when the system runs the simulation or imposed on the calculation.

When the first rate process statement is found (see list of possible statements above and FIG. 8), each species or temperature involved in the rate process will be internally assigned a differential equation and the appropriate source or sink term will be internally added to that equation. As additional rate processes are defined proceeding down the process sheet of FIG. 8, existing equations are appended with sources and sinks as necessary and new equations created as necessary until the bottom of the process sheet is reached. The model is now ready for the first timestep.

Phases, flows and rate process statements may appear in any order on the process sheet 2(*b*) of FIG. 8, as long as each phase mentioned in a rate process has been added to the phase database earlier in the process sheet. Components mentioned on the process sheet 2(*b*) must be listed on the components sheet 2(*a*). Rate terms implied by the rate process statements are calculated at every timestep in the order in which their statements appear on the process sheet 2(*b*). Only phases, flows, rate processes and parameters defined on the process sheet may be subsequently used to define initial conditions, parameter values and profiles on the scenarios and data sheets.

The user can view the validated model as a set of equations linked with the parameters. The following illustrates generic aspects of such a model, which contains several different types of phase and rate process.

```
Components (4)
     A            52 g/mol
     hydrogen      2 g/mol
     Product     175 g/mol
     solvent      60 g/mol
     UNIFAC used for components
Phases (5)
     Liquids (fixed density)
          Organic (liquid) contains solvent
                user Variables in phase: m0, m1, m2
          tank contains Product, solvent
          Equations:
                Density = initial value user specified
                Mass = Σ(n i.MW i)
                Volume = mass/density
                Nmoles = Σ(n i)
     Liquids (fixed volume)
          Bulk liquid contains A, B, P
          Equations:
                Volume = user specified
                mass = Σ(n i.MW i)
                density = mass/volume
                Nmoles = Σ(n i)
     Solids
          Crystals contains Product
          user Variables in phase: Cmz, Csol, Cprod
          Equations:
                Density = user specified
                Mass = Σ(n i.MW i)
                Volume = mass/density
                Nmoles = Σ(n i)
     Gases (fixed pressure)
          Sparge contains hydrogen
          Equations:
                Pressure, P = user specified
                Mass = Σ(n i.MW i)
                Density = mass.P/(Nmoles RT)
                Volume = Nmoles RT/P
                Nmoles = Σ(n i)
     Gases (fixed volume)
          Sparge contains hydrogen
          Equations:
                Volume, V = user specified
                Mass = Σ(n i.MW i)
                Density = mass /V
                Pressure = Nmoles RT/V
```

```
-continued

Nmoles = Σ(n i)
Flows (5)
     Liquids
          flow1 contains A, solvent
          flow2 contains B, solvent
          flow3 contains water
          Equations:
                Density = user specified
                Mass flow = Σ(n i, flow.MW i)
                Q = mass flow/density
                Nmole flow = Σ(n i, flow)
     Solids
          flow5 contains seed
          Equations:
                Density = user specified
                Mass flow = Σ(n i, flow.MW i)
                Q = mass flow/density
                Nmole flow = Σ(n i, flow)
     Gases
          flow4 contains hydrogen
          Equations:
                mass flow = Σ(n i, flow.MW i)
                Density = mass flow P/(Nmole flow RT)
                Q = mass flow/density = Nmole flow RT/P
                Nmole flow = Σ(n i, flow)
     Transfer to
          Bulk liquid (phase1) from tank (phase2) using flow4
          Equations:
                Rate to phase1 & from phase2 = volume flow.(n i)/
                  volume2
                Rate of cooling of phase1 [W] =
                  mcp.flow.(Tphase − Tflow)
                Rate of change of phase1 CP given by mixing rules
                Rate of change of phase1 Density given by mixing
                  rules
     Feed
          flow1 to bulk liquid
          flow2 to bulk liquid
          Equations:
                Rate to phase = molar flow of component
                Rate of cooling of phase [W] = mcp.flow.(Tphase −
                  Tflow) + |Hmix.Q
                Rate of change of phase CP given by mixing rules
                Rate of change of phase Density given by mixing
                  rules
     Remove
          flow3 from bulk liquid
          Equations:
                Rate from phase = (n i)/tres, or volume flow*(n i)/
                  volume
Reactions (3)
     Bulk liquid
          A + B > Product (Reaction1)
          P + 2B = C (Reaction2)
          Equations:
A + B = Product dHr = −160 kJ/mol
rate> = V.k[A]^1.[B]^1 where k = kref exp[−Ea/R(1/T − 1/Tref)]
rate< = V.k[Product]^1 where k = kref exp[−Ea/R(1/T − 1/Tref)]
P + B = 2C dHr = −250 kJ/mol
rate> = V.k[P]^2.[B]^0 where k = k0 exp(−Ea/RT)
rate< = V.k[C]^2 where k = k0 exp(−Ea/RT)
Heat output for reaction i [W] = (rate>_i − rate<_i) * −dHr_i
Heat release in phase, Qr [W] = Σ[(rate>_i − rate<_i) * −dHr_i]
     Organic
          A + B > Product (Reaction3)
          Equations:
A + B > Product dHr = −160 kJ/mol
rate> = V.k[A]^1[B]^1 where k = kref exp[−Ea/R(1/T − 1/Tref)]
Heat output for reaction i [W] = (rate>_i − rate<_i) * −dHr_i
Heat release in phase, Qr [W] = Σ[rate>_i − rate<_i) *
  −dHr_i]
```

The following is part of a sample middle (Example 1) illustrating the equations set up for two liquid phases and the rate process of mass transfer between the phases and chemical reactions in one of the phases.

| Components (7) |
| --- |
| heptane 100 g/mol |
| water 18 g/mol |
| A 100 g/mol |
| B 117 g/mol |
| P 100 g/mol |
| D 117 g/mol |
| OH 17 g/mol |

| Phases (2) |
| --- |
| Liquids (set density) |
| Organic contains: A, P, heptane |
| Aqueous contains: water, A, P, D, OH |
| Equations: |
| Density = initial value user specified |
| Mass = $\Sigma(n_i.MW_i)$ |
| Volume = mass/density |
| Nmoles = $\Sigma(n_i)$ |

| Reactions (2) |
| --- |
| Aqueous |
| A + OH > P    (Rxn1) |
| P + OH > D    (Rxn2) |
| Equations: |
| A + OH = P    dHr = 0 kJ/mol |
| rate> =V.k$[A]^1$.$[OH]^1$ |
| where k = kref exp[-Ea/R(1/T − 1/Tref)] |
| P + OH = D    dHr = 0 kJ/mol |
| rate> = V.k$[P]^1$. $[OH]^1$ |
| where k = kref exp[-Ea/R(1/T − 1/Tref)] |
| Heat output, reaction i [W]= (rate>_i-rate<_i)*-dHr_i |
| Heat release in phase, Qr [W]= $\Sigma$[(rate>_i-rate<_i)*-dHr_i] |

| Mass Transfer (1) |
| --- |
| Mass transfer between organic and aqueous: |
| of A (using Cd/Cc) |
| of P (using Cd/Cc) |
| Equations: |
| Continuous phase (c) = bulk liquid |
| Dispersed phase (d) = organic |
| Rate of mass transfer from dispersed to continuous phase |
| [mol/s] = K_CD.ad(Cc*-Cc) .Vd |
| where 1/K_CD = 1/kc + 1/kd.sCD and Cc* = Cd/SCD |
| SCD is the partition coefficient (Cd/Cc) at equilibrium |
| between the phases |
| A: SCD given by Cd/Cc |
| P: SCD given by Cd/Cc |

Initial values for all differential equations may be further set and/or overridden on the scenarios sheet 2(*c*), as may the values of parameters used in calculation of rate processes. This is desirable since the scenarios sheet 2(*c*) allows the creation of several copies of the model (one per row) that differ in initial conditions (e.g. recipe) and parameter values (e.g. heat removal capacity).

Profiles for any variable or parameter may be entered on data sheets associated with the scenarios defined. These profiles may be passive (i.e. measured responses or inputs that may be compared with values calculated by the model) or active (i.e. imposed on the model, overriding any calculations of those variables by the model). The latter would be the case e.g. in a model of an experiment in which the feed rate or temperature was known to have followed a particular profile.

Only data sheets 2(*d*) referenced on the scenarios sheet 2(*c*) will be read into the system.

25: Test Model

A simulator function of the system executes and integrates the equations in a manner ensuring that the transfer rates between phases of the various parameters are consistent. The basic requirement is that there is mass and energy conservation between the phases and rate processes are consistent in the model. The user may follow the progress of the simulation in a chart (FIGS. 13 and 14), table or dynamic snapshot (FIG. 15) of the whole system at any time, thereby identifying potential inconsistencies in the model set-up.

Integration of the equations in the simulator allows the profiles of each variable to be calculated as a function of time since the start of the simulation. On each time step, including the first, all sources and sinks in the equations are calculated using the values at the start of the step. These rates are then applied to calculate the value after a timestep, dt. The timestep is chosen such that an acceptably small numerical error will occur and if this is not achieved, the timestep is reduced and the step repeated until it is.

The system contains multiple, purpose-developed equation solvers, e.g. Backwards Euler, LSODA and Rosenbrock. Each has been specially adapted to meet the demands of an industrial process simulation tool, i.e. flexibility, robustness and reliability over a very broad range of conditions, for example:

careful initialisation of the model integration, typically during the first few seconds of a simulation, in order to capture the details of rapid processes which can significantly affect the subsequent course of the run, e.g. equilibration of ionic component concentrations at the start of a batch;

prevention of unphysical results such as negative values of species concentration;

capability to handle 'stiff' systems, i.e. where individual rate processes affecting a single equation differ by many orders of magnitude;

optimisation of run time by switching between 'stiff' solving and 'non-stiff' solving as required by the integration task undertaken without losing accuracy;

automatic reporting from the solver to the user on which of the multiple equations being solved is the slowest, i.e. limiting the overall speed in reaching a solution.

26: Find Best Fit Parameters

This is an automated iterative step performed by a fitting function in which the model is successively executed exclusively with the data of the edited and validated model until the model outputs match the experimental results as inputted in the data files 2(*d*). All parameter changes are by the fitting function and may follow an automated parameter fitting algorithm with repeated automatic execution until a desired degree of fit of physical and chemical rate constants is achieved or the number of permitted iterations is exceeded. Some advantageous aspects of the fitting function relate to the streamlining of workflow for the user, particularly with respect to the levels of flexibility to manage the experimental data that will be fitted to. Thus, within a single user session:

the whole of a data series or only a part of the series can be fitted to (Level 1);

multiple data series within a single experiment can be fitted to (Level 2);

multiple data sets for any number of experiments can be fitted to (Level 3);

the user can reset and rerun a fitting exercise using any combination of adjustments to the data provided by Levels 1, 2 and 3;

the user can introduce relevant data in staged manner as it is required, so that even very sophisticated strategies for obtaining and building up a set of fitted parameters in complex systems can be achieved; and the user can undertake a fitting exercise without recourse to a separate data import step since the modelling system carries the experimental data with the model.

The selection/deselection of the parameters to be fitted (e.g. kinetic rate constants) is equally flexible in allowing the user to switch on and off parameters whilst following a strategy without having to re-launch an exercise or the application. The fitting module has an advantageous aspect in that both scale-dependent parameters (vessel parameters) and scale-independent parameters (reaction kinetics) can be fitted in the same model.

Integrity of the model is assured because the fitting function only uses input data which has been received by the model editor and processed by the validation function.

27: Find Process Optimum

In this step an optimisation function of the system receives from the user, via the natural language on the process sheet, a definition of the parameter to be maximised or minimised or automatically selects such a parameter. Where the parameter is user inputted, the definition uses the Variables and Calculate natural language of FIG. 12. For example, if the user wishes to maximise process yield, the optimisation module executes the model simulator many times to determine the maximum yield and the values of the model parameters, i.e. recipe and vessel operating conditions, required to achieve this. The user typically validates this result by carrying out an actual experiment with the parameter values indicated by the model, but has saved material and many days or weeks of laboratory or plant time in not undertaking many 'dead-end' experiments that would give sub-optimal results.

This step represents the first significant predictions of the modelling system, as up to now, it has been used to develop a better understanding (which phases, rate processes are involved) of the user's problem, but now it is simulating conditions for which no data yet exists. The system is designed so that users reach this step as quickly as possible, by following the workflow and procedure facilitated by the system as shown in FIG. 3. The time taken to reach this point and predict the optimum can be a small fraction of the time needed to conduct an experimental programme of similar scope, hence one of the major benefits of the invention.

28: Update Model

The user inputs may update the model within the executable and/or by making the required amendments to the spreadsheet files 2(a) to 2(d) to update the model for the desired parameter fit or optimum output in 27 and 28, as well as any new experimental data.

29: Use Model

The model may then be executed for each of a number of "what if" inputs by the user. For example, the user may wish to determine what happens if the quantity of catalyst is reduced, or an alternative vessel or operating condition is used for the synthesis step. The user may set up the required additional scenarios for these cases by appending them (copying rows) in the scenarios file, then launching the external executable of the system and simulating the new cases either all at once or in sequence. As in 27 above, the system is now making predictions with the model for conditions where no data yet exist. Such predictions guide the user towards a more predictable, robust set of conditions and help to anticipate problems that have not yet occurred by rapid usage of the system to define the satisfactory operating envelope. The time and material savings resulting from this capability of the system are two of the major benefits of the invention.

30: Check Vessel Fit

FIG. 16 shows a vessel assessment function that generates an output of suitability of the intended vessel for the modelled process and conditions on the basis of geometry and operating conditions such as agitator rotational speed. This element of the system is based on validated empirical data and provides assurance that the model calculations in steps 21 to 29 produce a practically feasible process to operate in standard multi-purpose equipment available for these applications. Such calculations are strongly advised within the system and ensure that modelling is carried out in a responsible way, with end results in the real world that accord with model predictions.

31: Generate Reports/32: Archive Project Results

The outputs of operation of the model may be written by the system to reports, which may be archived according to an archive configuration.

It will be appreciated that the system allows scale-up, optimisation and trouble-shooting of synthesis reaction and workup steps in the pharmaceutical, fine chemicals, agrochemicals and other chemical industries. Non-specialist users are able to quantify process rates, especially chemical kinetic and equipment-related parameters, without having to write and solve equations. The following are some specific application areas of the invention:

In solution chemistry, the system uses kinetics to help find a better set of operating conditions (e.g. recipe, temperature) using fewer lab tests than a Design of Experiments (DOE) study.

In exothermic reactions, the system uses kinetics and heat balances to help design a safe process, including feed profile and agitation conditions.

In crystallisation (all types), the system uses the relative rates of supersaturation and de-supersaturation to help develop a scalable process avoiding 'fines', including a seeding strategy (e.g. timing, quantity).

In dosing-controlled reactions, the system uses micromixing rates to help avoid local hotspots or high concentrations.

In hydrogenations, the system helps balance gas supply and mass/heat transfer rates with the kinetics of reactions occurring on the catalyst surface, including poisoning and deactivation.

In product engineering, the system enables formulations to be developed and optimised for optimal performance in end use; e.g. excipient levels in a pharmaceutical dosage form can be found which optimise the rate of release of active drug substance in a USP dissolution apparatus intended to replicate conditions in the human stomach; in this case, the defined phases include the layers of excipients and the liquid in the dissolution apparatus; mass transfer occurs between these phases; other user-defined rate processes may also be added; these mechanisms are represented on the process sheet using the natural language and chemical species properties are specified on the components sheet.

The modelling system can be applied to predict dissolution from a specified drug delivery system or solid dosage form in vitro, in the paddle dissolution apparatus. Variations of the model, available from a stored library, would be for different systems in different types of dissolution apparatus.

The model can take account of the following variables and predict how they will influence the release/dissolution of the drug (active ingredient) from the dosage form:

i) Effect/influence of the physicochemical properties of active ingredient itself:

e.g.: solubility; diffusion coefficient; pKa; particle size ii) Effect/influence of excipients:
- e.g.: swelling and simultaneously eroding polymer; acid/basic excipients which can alter the microenvironmental pH; disintegrants; lubricants; fillers; pore-forming excipients; surfactants which can alter the wettability of the dosage form and the solubility of the active ingredient; and effect of altering excipient particle size.

iii) Effect of changes in the shape of the dosage form:
- e.g. as a result of: dissolution; swelling/erosion; disintegration.

iv) Effect of changes in the hydrodynamics of the dissolution assembly:
- e.g. different rotation speeds of the paddle v) Effect of changes in the dissolution medium
- e.g.: pH; buffer capacity; ionic strength; viscosity; inclusion of additives such as surfactants etc.

In product engineering, the system enables formulations for the delivery of an agrochemical such as an insecticide to be optimised with respect to e.g. solution make-up, level of additives, pH, such that active ingredient will be delivered in end use for maximum effect; in this case, the defined phases include the liquid and solid phases and the rate processes may include chemical reactions, mass transfer and heat transfer; other user-defined rate processes may also be added; these mechanisms are represented on the process sheet using the natural language and chemical species properties are specified on the components sheet.

In product engineering, the system enables shelf-life predictions to be made based on various product formulations and those formulations to be adapted depending on e.g. climatic conditions entered as active temperature profiles on a data sheet.

The system may be applied as described herein to processes in the following industries, among others: pharmaceutical and agrochemical active ingredient supply, product engineering and formulation, food processing, paper making, paint manufacture, polymer manufacture and processing, water quality and supply and effluent treatment.

It will be appreciated that the natural language is extensible and is continually evolving to include additional mechanisms and specific parameters as required to model applications that arise, such as various types of nucleation, particle growth, agglomeration, breakage and diffusion. Each of these additions to the natural language operate in the same way as those exemplified here, with corresponding equations automatically modified when they are found on the process sheet.

An important aspect of the system to achieve this is a powerful chemical kinetics and multi-phase system differential equation solver. The solver contains a number of integration methods that are robust and fast when applied to both stiff (typical of chemical kinetic) and non-stiff systems. It has been specially adapted to be robust and reliable over a very broad range of conditions, for example, preventing negative values of species concentrations.

A spreadsheet application is used as a 'database' file, to facilitate data entry by users in a familiar environment and easy distribution of models and results. Users enter their data and a text-based description of their process and conditions in a natural language (using terms like 'Phase', 'Flow', 'Reactions in', 'Heat Transfer', etc.) None of the spreadsheets' equation solving capabilities are used by the system, it merely reads the content describing the user's data and process details. Natural language refers to the use of words to represent any physicochemical rate process that can be described by an ordinary differential equation. When the sheets are read into the system, the required differential equations are built automatically. During simulation, time steps continuously adapt to the current gradients in concentration, temperature or other dynamic variables so that mass, energy and e.g. particle number conservation equations are accurately obeyed. There is effectively no limit on the number of reaction steps, phases (gas, liquid, solid), feeds or other rate processes that may be simulated with the system.

It will be appreciated that, with the modelling system, i) models can be built in a matter of minutes by non-specialist chemist or engineer users, ii) modelling results in significant time savings in process development relative to experimentation alone; iii) that modelling results in a reduced requirement for material to be used in tests, especially in early stage development when material is scarce and expensive; iv) the system can be used to trouble-shoot and optimise existing commercial processes, for example, drugs that have been scaled-up poorly, can deliver significant cost savings via increases in productivity and the meeting of production schedules.

Within the system, non-specialist and occasional users can:
- open and run scenarios;
- plot and tabulate results;
- test their ideas, e.g. by changing parameters and profiles interactively;
- fit parameters such as reaction kinetics, mass transfer coefficients, heat transfer coefficients; and
- export results back to spreadsheets, presentation or word processing systems.

Other advantageous aspects of the system include:
- the capability for fitting of chemical kinetics to multiple experimental profiles/responses and multiple experiments;
- the workflow of the fitting exercise has been streamlined so that the user can undertake an exercise without recourse to a separate data import step;
- a library of template models and utilities for use with equipment and data used in chemical development:
  - e.g. MultiMax, LabMax, RC1 vessels
  - combination of FT-IR, Qr and sample data in the same model
  - making use of IR, XRD, FBRM data for crystallisation modelling;
- direct input of concentration data and/or mass data in the model;
- easy input of solubility data for phase transfer reactions;
- comprehensive access to and flexibility with reaction parameters;
- an intuitive user interface, with spreadsheet look and feel;
- the capability to run a model from anywhere on a network;
- powerful automated fitting module based on state of the art of algorithms incorporating:
  - estimation of kinetic parameters (rate constant at reference temperature k, Arrhenius preexponential factor k0, activation energy Ea, heat of reaction, reaction orders)
  - estimation of equipment parameters (e.g. mass transfer coefficient kLa, heat transfer coefficient U) for physical processes
  - greater manipulation of data read from the spreadsheet, such as incorporating experimental error and user weighting on data sets, fit to initial part of run
  - fitting to data from multiple experiments
  - dynamic simulation of data with fitted parameters to show goodness of fit;
- comprehensive handling of properties for mixing of phases;
- comprehensive access to model parameters;

readymade templates and supporting utilities for all common reaction, workup and isolation steps in the manufacture of drug substances and other chemicals;

content organised to suit best practise chemical/process development and scale-up workflow;

on-line training content and exercises for new users;

comprehensive crystallisation and hydrogenation libraries; and comprehensive vessel mixing and heat transfer utilities.

The invention is not limited to the embodiments described but may be varied in construction and detail.

The invention claimed is:

1. A physicochemical process modelling system comprising a data processor, a user input interface, an output interface, a memory, and a data storage device, wherein, the storage device stores a library of initial models each having code for modelling a physicochemical process, said initial model library having a hierarchical structure with initial models at leaf nodes of the structure and physicochemical selection criteria at upper levels of the structure;

the processor is programmed with:
  a model editor having an input interface for prompting user input of chemical species component data, a process description, and experimental data, the process description being in a natural language,
  a validation function for parsing the inputs, for performing semantic, contextual, consistency, and tolerance checks, and for automatically building equations according to rules associated with the process description,
  a simulator function for executing and integrating the equations built by the validation function,
  a fitting function for operating exclusively with data of the edited and validated model to fit physical and/or chemical rate constants to achieve a best fit with the experimental data, and
  an optimisation function for iteratively executing the fitted model with different process condition inputs until an output parameter is optimized; and the output interface outputs a simulation of a modelled physicochemical process to a user.

2. The system as claimed in claim 1, wherein the model editor interface receives the component, process, and experimental data in separate but linked input files.

3. The system as claimed in claim 1, wherein the model editor interface receives the component, process, and experimental data in separate but linked input files; and wherein the model editor interface also receives a scenarios input file specifying options for implementing specific cases of the generic process input file.

4. The system as claimed in claim 3, wherein each record of the scenarios file specifies a combination of vessel parameters and values of temperature, pressure and process constituents.

5. The system as claimed in any of claim 1, wherein the model editor interface receives the component, process, and experimental data in separate but linked input files; and wherein the experimental data file is linked to the other files, and the model editor uses the data from the experimental data file in preference to data of the other files.

6. The system as claimed in claim 1, wherein the model editor interface provides a dictionary of phrases having meanings recognised by the system, and performs user interfacing to cut and paste phrases into the process description.

7. The system as claimed in claim 6, wherein the phrases include phrases identifying a rate of change, or a type of phase or flow for physicochemical process modelling.

8. The system as claimed in claim 1, wherein the model editor interface allows user setting of attributes of variables including:
  a plot attribute, causing the associated variable to be plotted during modelling, and
  an impose attribute, causing the associated variable to be treated as data which participates in the execution of a model and includes imposed operating conditions.

9. The system as claimed in claim 1, wherein the validation function builds equations describing the physicochemical process by:
  parsing the inputted components and building a database of valid component names and properties;
  parsing phase data of the process description and building a database of valid phase names and states;
  parsing flow statements of the process description and building a database of valid flow names and states, and
  automatically assigning a differential equation to each component or temperature involved in the process description and adding a corresponding source term or sink term to the equation.

10. The system as claimed in claim 9, wherein the validation function stores a validated model as the developed equations with parameters from the component and process description received by the model editor.

11. The system as claimed in claim 3, wherein the model editor interface receives the component, process, and experimental data in separate but linked input files; and wherein the model editor interface also receives a scenarios input file specifying options for implementing specific cases of the generic process input file; and wherein the validation function stores a validated model with a plurality of input conditions in a scenarios file with its associated experimental data.

12. The system as claimed in claim 9, wherein the validation function recognises flow and phase inputs by parsing predefined statements followed by flow or phase inputs.

13. The system as claimed in claim 1, wherein the simulator function integrates the equations of a validated model by ensuring that there is mass and energy conservation in the model and that rates are consistent; and wherein the simulator calculates all source terms and sink terms of each equation at each of a plurality of time steps.

14. The system as claimed in claim 1, wherein the simulator function comprises a plurality of solver algorithms, each suitable for a particular validated model.

15. The system as claimed in claim 1, wherein the fitting function selects to fit model parameters to the whole, only part of, or multiple series of experimental data.

16. The system as claimed in claim 1, wherein the fitting function selects to fit model parameters to the whole, only part of, or multiple series of experimental data; and wherein the fitting function resets in response to a user input and re-executes using experimental data received by the model editor and validated by the validation function.

17. The system as claimed in claim 1, wherein the fitting function operates ignoring parameters which are indicated as being switched off in the process description.

18. The system as claimed in claim 1, wherein the system further comprises a vessel fit function for assessing suitability of a vessel for the physicochemical process being modelled according to vessel characteristics.

19. A physicochemical process modelling process carried out by a data processor, a user input interface, an output interface, a memory, and a data storage device, wherein, the storage device stores a library of initial models each having code for modelling a physicochemical process, said initial model library having a hierarchical structure with initial models at leaf nodes of the structure and physicochemical selection criteria at upper levels of the structure, in the processor:

a model editor prompts user input of chemical species component data, a process description, and experimental data, the process description being in a natural language, a validation function parses the inputs, performs semantic, contextual, consistency, and tolerance checks, and automatically builds equations according to rules associated with the process description, a simulator function executes and integrates the equations built by the validation function, a fitting function operates exclusively with data of the edited and validated model to fit physical and/or chemical rate constants to achieve a best fit with the experimental data, and an optimisation function iteratively executes the fitted model with different process condition inputs until an output parameter is optimised; and the output interface outputs a simulation of a modelled physicochemical process to a user.

20. A physicochemical process modelling system comprising a data processor, a user input interface, an output interface, a memory, and a data storage device, wherein, the storage device stores a library of initial models each having code for modelling a physicochemical process;

the processor is programmed with:

a model editor having an input interface for prompting user input of chemical species component data, a process description, and experimental data, the process description being in a natural language, a validation function for parsing the inputs, for performing semantic, contextual, consistency, and tolerance checks, and for automatically building equations according to rules associated with the process description, a simulator function for executing and integrating the equations built by the validation function, a fitting function for operating exclusively with data of the edited and validated model to fit physical and/or chemical rate constants to achieve a best fit with the experimental data, and an optimisation function for iteratively executing the fitted model with different process condition inputs until an output parameter is optimised;

wherein the validation function builds equations describing the physicochemical process by:

parsing the inputted components and building a database of valid component names and properties;

parsing phase data of the process description and building a database of valid phase names and states;

parsing flow statements of the process description and building a database of valid flow names and states, and automatically assigning a differential equation to each component or temperature involved in the process description and adding a corresponding source or sink term to the equation; and the output interface outputs a simulation of a modelled physicochemical process to a user.

21. A physicochemical process modelling system comprising a data processor, a user input interface, an output interface, a memory, and a data storage device, wherein, the storage device stores a library of initial models each having code for modelling a physicochemical process;

the processor is programmed with:

a model editor having an input interface for prompting user input of chemical species component data, a process description, and experimental data, the process description being in a natural language, a validation function for parsing the inputs, for performing semantic, contextual, consistency, and tolerance checks, and for automatically building equations according to rules associated with the process description, a simulator function for executing and integrating the equations built by the validation function, a fitting function for operating exclusively with data of the edited and validated model to fit physical and/or chemical rate constants to achieve a best fit with the experimental data, and an optimisation function for iteratively executing the fitted model with different process condition inputs until an output parameter is optimised;

the simulator function integrates the equations of a validated model by ensuring that there is mass and energy conservation in the model and that rates are consistent; and wherein the simulator calculates all source terms and sink terms of each equation at each of a plurality of time steps; and the output interface outputs a simulation of a modelled physicochemical process to a user.

22. A computer program product comprising software code for executing on a digital computer, said software code being programmed to carry out a physicochemical process modelling process using a data processor, a user input interface, an output interface, a memory, and a data storage device, wherein, the storage device stores a library of initial models each having code for modelling a physicochemical process, said initial model library having a hierarchical structure with initial models at leaf nodes of the structure and physicochemical selection criteria at upper levels of the structure, in the processor:

a model editor prompts user input of chemical species component data, a process description, and experimental data, the process description being in a natural language, a validation function parses the inputs, performs semantic, contextual, consistency, and tolerance checks, and automatically builds equations according to rules associated with the process description, a simulator function executes and integrates the equations built by the validation function, a fitting function operates exclusively with data of the edited and validated model to fit physical and/or chemical rate constants to achieve a best fit with the experimental data, and an optimisation function iteratively executes the fitted model with different process condition inputs until an output parameter is optimised; and the output interface outputs a simulation of a modelled physicochemical process to a user.

* * * * *

UNITED STATES PATENT AND TRADEMARK OFFICE
CERTIFICATE OF CORRECTION

PATENT NO. : 7,599,822 B2
APPLICATION NO. : 11/197370
DATED : October 6, 2009
INVENTOR(S) : Hearn et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1097 days.

Signed and Sealed this

Twenty-eighth Day of September, 2010

David J. Kappos
*Director of the United States Patent and Trademark Office*